(12) United States Patent
Fyles et al.

(10) Patent No.: US 6,518,309 B1
(45) Date of Patent: Feb. 11, 2003

(54) MICROBIOCIDAL PROPERTIES OF POY-SUBSTITUTED GUANIDINIUM SALTS

(75) Inventors: Thomas M. Fyles; Robert D. Rowe, both of Victoria (CA)

(73) Assignee: RhoCraft Research and Development Ltd., Victoria (CA)

( * ) Notice: Subject to any disclaimer, the term of this patent is extended or adjusted under 35 U.S.C. 154(b) by 0 days.

(21) Appl. No.: 09/548,666

(22) Filed: Apr. 13, 2000

Related U.S. Application Data

(60) Provisional application No. 60/129,246, filed on Apr. 14, 1999.

(51) Int. Cl.[7] ............... A01N 33/00; A01N 37/52; A61K 31/13; A61K 31/155
(52) U.S. Cl. .................. 514/579; 514/634
(58) Field of Search .................. 514/634, 579

(56) References Cited

U.S. PATENT DOCUMENTS 4,368,053 A * 1/1983 Eckhardt et al. ............... 8/102

FOREIGN PATENT DOCUMENTS

| DE | 2144125 | | 3/1973 |
|---|---|---|---|
| GB | 1 091 049 | | 11/1967 |
| GB | 1249468 | * | 10/1971 |
| JP | 63-281502 | | 11/1988 |

OTHER PUBLICATIONS

El–Din et al, Structure–activity relationships, 1977, Meded. Fac. Landbouwwet., Rijksuniv. Gent, vol. 42 (2, Pt. 1), pp. 1017–1025.*

English–language abstract of JP 04 225945, Patent Abstracts of Japan, vol. 016, No. 575, August 14, 1992.

PCT International Search Report mailed on Oct. 23, 2001 for International application No. PCT/CA01/00112.

* cited by examiner

*Primary Examiner*—Alton Pryor
(74) *Attorney, Agent, or Firm*—Klarquist Sparkman LLP

(57) ABSTRACT

This patent discloses the use of poly-substituted isothiouronium salts (T1 where $R_1$, $R_2$, $R_3$, $R_4$=hydrogen, alkyl, cycloalkyl, alkenyl, cycloalkenyl, aryl, heteroaryl, etc. and $X^-=Cl^-, Br^-, NO_3^-, CH_3CO_2^-$, or any other common anion), poly-substituted guanidinium salts (G1 where $R_1$, $R_2$, $R_3$, $R_5$, $R_6$=hydrogen, alkyl, cycloalkyl, alkenyl, cycloalkenyl, aryl, heteroaryl,etc. and $X^-=Cl^-, Br^-, NO_3^-, CH_3CO_2^-$, or any other common anion), or mixtures of two or more of the above compounds, as the biocidal component of microbiocidal or antifouling formulations.

19 Claims, No Drawings

MICROBIOCIDAL PROPERTIES OF POY-SUBSTITUTED GUANIDINIUM SALTS

This application claims benefit of No. 60/129,246 filed Apr. 14, 1999.

BACKGROUND

Surfaces exposed to humid and aqueous environments are readily colonized by microorganisms and may be further colonized by higher organisms. The resultant fouling has many adverse effects on these surfaces and the objects they compose. Current anti-fouling methods often involve the use of highly toxic and environmentally stable compounds, usually including a metal ion such as copper (as in $CuO_2$) or tin (as in tri-butyltin fluoride, TBTF). Research has shown that these heavy metals remain in the environment and retain their toxicity for many years. Furthermore, it has been demonstrated that these compounds become concentrated in plants and animals higher up the food chain with many adverse effects. These compounds, while effective as anti-fouling agents are under increasing pressure from environmental regulations that seek to limit the concentration of heavy metals in the environment. An effective anti-fouling agent with a short and known biological lifetime is therefore of great interest to the industry.

This invention describes the use of poly-substituted isothiouronium salts (T1), and poly-substituted guanidinium salts (G1). The biological activity of these classes of compounds has been recognized previously as variously fungicides, bactericides, lepidoptericides, antibiotics, etc. It is also known that isothiouronium salts (T1). and neutral isothioureas (T2) can be interconverted. Similarly, the interconversion of guanidinium salts (G1) and neutral guanidines (G2) is also well established. These pairs of compounds are related as acid and conjugate base, differing only in protonation state. Consequently, in many cases the biological activity of isothiouronium salts can be inferred from the known activity of isothioureas, and vice versa. Similarly the biological activity of guanidinium salts can be inferred from the known activity of neutral guanidines, and vice versa. This is particularly true when the compounds are dispersed in an aqueous environment.

Many authors have reported examples of the activity of isothiouronium salts and isothioureas. For example, U.S. Pat. No. 4,515,813 discloses the lepidoptericidal properties of isothiourea compounds. Fungicidal and bactericidal activity of this class of compounds were also noted. compounds. Fungicidal and bactericidal activity of this class of compounds were also noted. Similarly, the use of pyridyl thiouronium salts as fungicides are disclosed in U.S. Pat. No. 3,655,898, and related pyridyl thiouronium N-oxides are useful as wood preservatives as described in Japan Patent 53109903. German Patent 2637651 describes the use of S-(p-isopropylbenzyl)thiouronium chloride as one of the biocidal components in a water-based paint formulation. Marine antifouling activity by dissolved isothioureas is disclosed in Japan Patent 05163105.

Similarly, there are many examples of the biological activity of guanidinium salts and guanidines. Several naturally occurring toxins from marine organisms contain the guanidinium functional group, most notably tetrodotoxin. The best-known commercial example is dodecyl guanidinium acetate (dodine), widely used as a fungicide and bactericide to control scab on hard fruits. It is also used as an industrial biocide and preservative. Dodine also shows synergistic anti-fouling activity in conjunction with other well-known antifouling agents such as tributyltin oxide as reported by Evans, Callow and Wood (1986). Dodine, in conjunction with quaternary ammonium salts, is reported by Bidwell, Farris and Cherry (1995) to control the growth of zebra mussels and Asian clams (moluscicidal activity). Such soluble formulations have also been disclosed in U.S. Pat. No. 4816163, U.S. Pat. No. 4906385, and Canadian Patent No. 1269927. A method to prepare an antifouling coating from a mixture of dodine and additional biocides has been disclosed in Japan Patent No. 04225945.

BRIEF SUMMARY TO INVENTION

Most of the previously reported isothiouronium and guanidinium containing compounds are monosubstituted with a relatively low carbon-number substituent. Although this is appropriate for applications requiring soluble biocides, it is obvious to someone skilled in the art that a successful coating application in contact with water will require sparingly soluble biocides. Solubility can be limited by increasing the carbon number of a single substituent, or by increasing the number of similar sized substituents. The present invention discloses the utility of the second strategy.

A second issue, previously unrecognized, is the role that anion exchange capacity may play in biocidal activity. Prior discussion of the mode of action of biocidal formulations containing isothiouronium or guanidinium salts focussed on their detergent capabilities (references cited above). Our parallel work on the development of ion-exchange membranes for dissolved gas sensors (U.S. patent application Ser. No. 09/444,867) showed that guanidinium salts are effective agents for the exchange of hydroxide ions across membranes. In the context of biocidal activity, an anion exchanger would disrupt the normal ionic and pH balance across a cell membrane that would prove to be fatal for microorganisms.

This invention describes the synthesis of a series of poly-substituted isothiouronium of type T1 and poly-substituted guanidinium salts of type G1, via intermediate thioureas of type T3, their formulation in paints, and their activity in limiting the growth of marine organisms on the treated surfaces as a result of prolonged immersion in open seawater. In addition to the biocidal and anti-fouling activity disclosed below, compounds of types T1 and G1 posses two additional properties of significant utility. The first is that they are colorless, that is they do not absorb significant amounts of visible light. Thus they could be used to inhibit fouling on windows exposed to humid or aqueous environments. The second is that they degrade easily in a marine environment to produce benign by-products. Thus a buildup of these compounds in the environment will be avoided.

Structural Formulae

General Formulae of Compounds Discussed

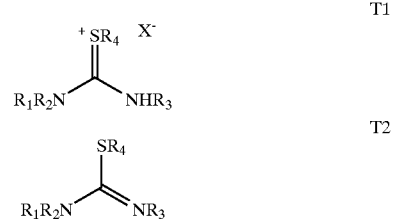

-continued

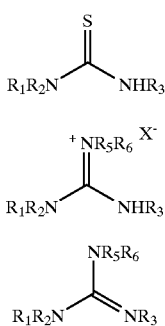

Reaction schemes:

Procedure A

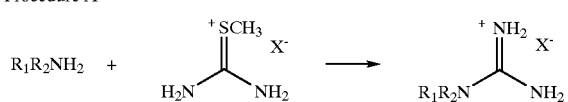

Procedure B

Procedure C

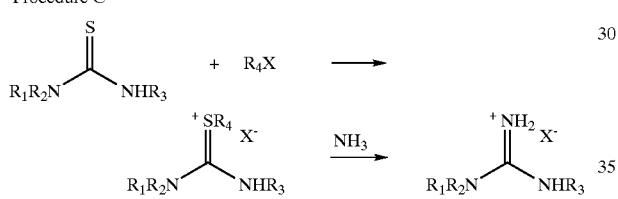

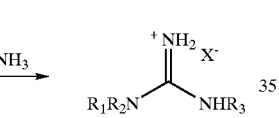

Procedure D

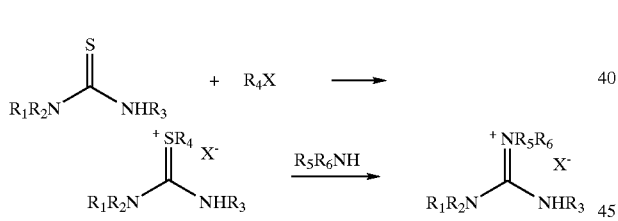

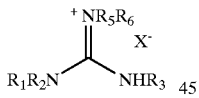

DETAILED DESCRIPTION OF THE INVENTION

Synthesis of Compounds

The synthesis of the various compounds is given in the reaction schemes in terms of a general procedure. The counterion produced in the synthesis is typically iodide that is subsequently exchanged for chloride or other anions by ion exchange. Procedure A can produce monosubstituted guanidium salts or N,N-disubstituted guanidinium salts, depending on the starting amine. Procedure B can produce N,N'-disubstituted thioureas or N,N,N' trisubstituted thioureas, depending on the starting amine. The first step of procedures C and D can produce N,N',S-trisubstituted isothiouronium salts or N,N,N',S-tetrasubstituted isothiouronium salts, depending on the starting thiourea. Direct reaction of isothiouronium salts with ammonia (procedure C) gives either N,N'-disubstituted guanidinium salts or N,N,N' trisubstituted guanidinium salts. Alternatively, reaction of isothiouronium salts with primary or secondary amines can (procedure D) can produce N,N',N"-trisubstituted guanidinium salts, N,N,N',N"-tetrasubstituted guanidinium salts, or N,N,N'N',N"-pentasubstituted guanidinium salts, depending on the starting isothiouornium salt and starting amine. A total of nine mono-, di-, and tri- substituted guanidinium salts (G1), and three tri-substituted isothiouronium salts (T1) were prepared by the methods shown.

All compounds were characterized by NMR, MS, and IR. By the methods disclosed below, the purity of the compounds was high without recourse to chromatographic separation. Samples of each compound were further purified by chromatography on silica. The purified materials all showed UV cutoff values below 300 nm, and showed an $\epsilon$ less than one at 300 nm for all compounds.

It will be obvious to someone skilled in the art that the nature of the substituent groups $R_1$, $R_2$, $R_3$, $R_4$, $R_5$, $R_6$ in structures T1 and G1 can be varied by judicious choice of starting amines and isothiocyanates according to the reaction schemes presented. The following general procedures, given for alkyl substituents, illustrate the methods used.

Procedure A (!!CAUTION!!: This procedure evolves methyl mercaptan. Use a hood. Avoid exposure.) An alkyl amine (1 eq.) and solid S-methyl isothiouronium iodide (2 eq.) were suspended in absolute ethanol (5–8 mL/g salt). The mixture was stirred at reflux under a reflux condenser. The evolution of methyl mercaptan was followed using moistened lead acetate test paper. The reaction was usually complete in 6 hours, but the reflux was continued overnight. The mixture was evaporated to a solid and redissolved in water. The water was extracted on a continuous extractor overnight using chloroform, the extracts were dried over magnesium sulfate, filtered and evaporated to yield the iodide salt of the product. The iodide was converted to the chloride using Amberlite IRA400 resin in methanol.

Spectroscopic data for compounds prepared by procedure A:

G1 where $R_1=C_{10}H_{21}$, $R_2=R_3=R_5=R_6=H$, $X^-=Cl^-$: $^1H$ NMR (CDCl$_3$, δ):0.95 (br. t., 3H), 1.54 (br. s., 14H), 1.60 (br. m., 2H), 3.10 (t., 2H), 4.90 (br. s., >5H); $^{13}C$ NMR (CDCl$_3$, δ):14.2, 22.7, 26.7, 28.5, 29.3 (m), 31.9, 42.5, 156.6; MS (+LSIMS, mNBA): 200.2 (M−Cl).

G1 where $R_1=C_{14}H_{29}$, $R_2=R_3=R_5=R_6=H$, $X^-=Cl^-$: $^1H$ NMR (CDCl$_3$, δ) 0.95 (br. t., 3H), 1.5 (br. s., 22H), 1.6 (br. m., 2H), 3.10 (t., 2H), 4.9 (br. s., >5H); MS (+LSIMS, mNBA): 256.2 (M−Cl).

G1 where $R_1=C_{18}H_{37}$, $R_2=R_3=R_5=R_6=H$, $X^-=I$: $^4H$ NMR (DMSO-d$_6$, δ): 0.95 (br. t., 3H), 1.54 (br. s., 30H), 1.60 (br. m., 2H), 3.10 (t., 2H), 4.90 (br. s., >5H); MS (+LSIMS, mNBA): 312.2 (M−I).

Procedure B (!!CAUTION!!: isothiocyanates are typically lachrymators. Use a hood. Avoid exposure.) An alkyl amine (1 eq.) and an alkyl isothiocyanate (1 eq.) were dissolved in toluene (5 mL/g amine). The mixture was stirred at reflux for 3–5 hr. The product precipitated in some cases. The mixture was concentrated under reduced pressure, cooled, and filtered. The precipitate was washed with pentane and air-dried. The product is sufficiently pure for the subsequent reaction.

Spectroscopic data for compounds prepared by procedure B:

T3 where $R_1=C_{10}H_{21}$, $R_2=H$, $R_3=C_4H_9$: $^1H$ NMR (CDCl$_3$, δ): 0.95 (m., 6H), 1.3 (br. s., 16H), 1.60 (m., 4H), 3.4 (br. s., 4H) 5.7 (br. s., 2H); $^{13}C$ NMR (CDCl$_3$, δ): 13.7, 14.1, 20.2 22.7, 26.9, 29.5 (m.), 31.0, 31.9, 44.0 (br.), 139.5; MS (+LSIMS, mNBA): 273.2 (M+H).

T3 where $R_1=C_{14}H_{29}$, $R_2=H$, $R_3=C_4H_9$: $^1H$ NMR (CDCl$_3$, δ): 0.95 (m., 6H), 1.3 (br. s., 24H), 1.60 (m., 4H), 3.4 (br. s., 4H), 5.7 (br. s., 2H); $^{13}C$ NMR (CDCl$_3$, δ): 13.7,14.1,20.2, 22.7, 26.9, 29.5 (m.), 31.0, 31.9, 44.0 (br.), 139.5; MS (+LSIMS, mNBA): 329.2 (M+H).

T3 where $R_1=C_{18}H_{37}$, $R_2=H$, $R_3=C_4H_9$: $^1H$ NMR (CDCl$_3$, δ): 0.95 (m., 6H), 1.3 (br. s., 32H), 1.60 (m, 4H), 3.4 (br. s., 4H), 5.7 (br. s., 2H); $^{13}C$ NMR (CDCl$_3$, δ): 13.7, 14.1, 20.2, 22.7, 26.9, 29.5 (m.), 31.0, 31.9, 44.0 (br.), 139.5 ; MS (+LSIMS, mNBA): 385.2 (M+H).

Procedure C (!!CAUTION!!: This procedure evolves methyl mercaptan. Use a hood. Avoid exposure.) A substituted thiourea (1 eq.) was suspended in absolute ethanol (5–10 mL/g, thiourea may not dissolve) and iodomethane (3 eq.) was added. The mixture was sealed in a low pressure hydrogenation bottle, stirred and heated to 80° C. After cooling, the vessel was opened and the unreacted iodomethane and solvent was removed by evaporation. The product at this stage is a isothiouronium salt of type T1 and may be worked up as indicated after the ammonia treatment below.

The product was dissolved in absolute ethanol (5 mL/g) and ammonia was added via a bubbler at a rate to allow dissolution. Ammonia addition was continued until a large excess was assured. The mixture was again sealed and heated at 80° C. for 24 hours. After cooling the vessel was opened (!!CAUTION!!: use a fume hood) and reheated to drive off the methyl mercaptan. The mixture was then evaporated to a thick oil. The oil was dissolved in water, extracted with methylene chloride, the extracts were dried over magnesium sulfate, filtered and evaporated to yield the iodide salt of the product. The iodide was converted to the chloride using Amberlite IRA400 resin in methanol.

Spectroscopic data for compounds prepared by procedure C:

T1 where $R_1=C_{10}H_{21}$, $R_2=H$, $R_3=C_4H_9$, $R_4$ CH$_3$, $X^-=Cl^-$: $^1H$ NMR (CDCl$_3$, δ): 0.9 and 0.95 (2 br. t., 6H), 1.2 (br. s., 16H), 1.6 (br. m., 4H), 2.8 (br. s. 3H), 3.75 (m, 4H), 7.8 (br. 2H); $^{13}C$ NMR (CDCl$_3$, δ): 13.7, 14.1, 19.8, 22.6, 27.0, 29.3 (m.), 31.8, 44.7, 45.0, 50.1, 166.5; MS (+LSIMS, mNBA): 287.4 (M−Cl).

T1 where $R_1=C_{14}H_{29}$, $R_2=H$, $R_3=C_4H_9$, $R_4$=CH$_3$, $X^-=I^-$: $^1H$ NMR (CDCl$_3$, δ): 0.9 and 0.95 (2 br. t., 6H), 1.2 (br. s., 24H), 1.6 (br. m., 4H), 2.8 (br. s. 3H), 3.75 (m., 4H), 7.85 (br. 1H), 8.4 (br., 1H); $^{13}C$ NMR (CDCl$_3$, δ): 13.7, 14.1, 19.7, 22.9, 27.1, 29.4 (m.), 31.8, 44.7, 45.1, 50.3, 166.5; MS (+LSIMS, mNBA): 343.4 (M−I) .

T1 where $R_1=C_{18}H_{37}$, $R_2=H$, $R_3=C_4H_9$, $R_4$ =CH$_3$, $X^-=Cl^-$: $^1H$ NMR (CDCl$_3$, δ): 0.9 and 0.95 (2 br. t., 6H), 1.2 (br. s., 32H), 1.6 (br. m., 4H), 2.8 (br. s. 3H), 3.75 (m. 4H), 8.0 (br. 2H); $^{13}C$ NMR (CDCl$_3$, δ): 13.7, 14.1, 19.7, 22.6, 27.1, 29.3 (m.), 31.8, 44.7, 44.8, 50.3, 166.5; MS (+LSIMS, mNBA): 399.4 (M−Cl).

G1 where $R_1=C_{10}H_{21}$, $R_3=C_4H_9$, $R_2=R_5=R_6=H$, $X^{-1}H$ NMR (CDCl$_3$, δ): 0.9 and 0.95 (2 br. t., 6H), 1.2 and 1.4 (br. s.+m., 16H), 1.6 (br. m., 4H), 3.15 (br. m., 4H), 6.4–7.0 (br., 4H); $^{13}C$ NMR (CDCl$_3$, δ): 13.7, 14.1, 20.0, 22.7, 26.8, 29.4 (m.), 31.9, 42.2, 42.5, 155.8; MS (+LSIMS, mNBA): 256.4 (M−Cl).

G1 where $R_1=C_{14}H_{29}$, $R_3=C_4H_9$, $R_2=R_5=R_6=H$, $X^{-1}H$, NMR (CDCl$_3$, δ): 0.9 and 0.95 (2 br. t., 6H), 1.2 and 1.4 (br. s.+m., 24H), 1.6 (br. m., 4H), 3.15 (br. m., 4H), 6.4–7.0 (br., 4H); $^{13}C$ NMR (CDCl$_3$, δ): 13.7, 14.1, 19.9, 22.7, 26.9, 29.4 (m.), 31.9, 41.8, 42.1, 156.2; MS (+LSIMS, mNBA): 312.5 (M−Cl).

G1 where $R_1=C_{18}H_{37}$, $R_3=C_4H_9$, $R_2=R_5=H$, $X^-=Cl^-$: $^1H$ NMR (CDCl$_3$, δ): 0.9 and 0.95 (2 br. t., 6H), 1.2 and 1.4 (br. s.+m., 32H), 1.6 (br. m., 4H), 3.15 (br. m., 4H), 6.4–7.0 (br., 4H); MS (+LSIMS, mNBA): 3.68.6 (M−Cl).

Procedure D

The procedure was identical to procedure C with the exception that an alkyl amine (2 eq.) was used in place of ammonia.

Spectroscopic data for compounds prepared by procedure C:

G1 where $R_1=Cl_{10}H_{21}$, $R_3=R_5=C_4H_9$, $R_2=H$, $X^-=Cl^-$: $^1H$ NMR (CDCl$_3$, δ): 0.95 (m., 9H), 1.2–1.4 (m., 18H), 1.6 (m., 6H), 3.25 (br. m., 6H), 7.0–7.2 (br., 3H); $^-$C NMR (CDCl$_3$, δ): 13.7, 13.8, 14.1, 19.9, 20.0, 22.7, 26.8, 29.4 (m.), 31.8, 31.9, 42.3, 42.6, 155.4; MS (+LSIMS, mNBA): 312.2 (M−Cl).

G1 where $R_1=C_{14}H_{29}$, $R_3=R_5=C_4H_9$, $R_2=R_6=H$, $X^-=Cl^-$: $^1H$ NMR (CDCl$_3$, δ): 0.95 (m., 9H), 1.2–1.4 (m., 26H), 1.6 (m., 6H), 3.25 (br. m., 6H), 7.0–7.2 (br., 3H); $^{13}C$ NMR (CDCl$_3$, δ): 13.7, 14.1, 19.9, 22.7, 26.8, 29.4 (m.), 31.8, 31.9, 42.5, 42.8, 155.7; MS (+LSIMS, mNBA): 368.6 (M−Cl).

G1 where $R_1=C_{18}H_{37}$, $R_3=R_5=C_4H_9$, $R_2=R_6=H$, $X^-=I^-$: $^1H$ NMR (CDCl$_3$, δ): 0.95 (m., 9H), 1.2–1.4 (m., 34H), 1.6 (m., 6H), 3.25 (br. m., 6H), 7.0–7.2 (br., 3H); $^{13}C$ NMR (CDCl$_3$, δ): 13.7, 14.1, 19.9, 22.7, 26.8, 29.4 (m.), 31.8, 31.9, 42.5, 42.8, 154.6; MS (+LSIMS, mNBA):.324.7 (M−I).

Assessment of Marine Antifouling Activity

An experiment was designed to follow the onset and development of algal growth on painted panels held approximately 1 m below the surface in open seawater. The apparatus consisted of a moored floating superstructure with a set of test panels suspended below it. The superstructure allowed the test panels to be lifted from the water periodically to assess the extent of growth and to photograph the panels. The apparatus was designed to hold 90 test panels each 10 cm square. The experiment examined nine of the compounds prepared, at two different dose levels (5 and 10 wt %) in three different topside marine paints (9×2×3=54 primary samples). None of the paints contained any commercial antifouling agent. A total of 12 control samples were included: 6 which were not touched, and 6 which were used for scrapes to examine the type of organisms populating the surface fouling layer. The remaining 24 test panels were assigned to randomized replicates of the primary samples, in sets of 8 for each paint type. The locations of the controls were fixed on the six arrays and the remaining 78 test panels were randomly assigned to the other locations.

The lexan test panels were sandblasted to provide a surface for paint adhesion, cleaned in methanol, and then in trifluorethanol immediately prior to painting. Paint samples were prepared from a weighed amount of the test compound and a known volume of paint using the measured paint density to arrive at the nominal 5 and 10 wt % dose levels. In most cases the compounds were dissolved in a few mL of methylene chloride before the paint was added. The paint samples were mixed by hand until homogeneous to the eye. A measured volume of the paint sample was spread on the cleaned test panel with a silk-screen tool using a jig designed to form a 250 μm paint layer. The painted test panels were then glued in place on the array and allowed to air dry for 72 hours. After painting, the sole identifier for the compound and formulation was from the array coordinates. Given that the six arrays were virtually indistinguishable after drying, the specific location of any particular compound was essentially hidden from the subsequent observers.

The experiment was initiated in the summer of 1999. Qualitatively, the panels remained clean for the first two weeks, then rapidly fouled over the next two weeks. By the end of a six-week period, the late-summer die-off of marine flora was evident from the amount of plant debris in the water column and the exposure of some previously fouled surfaces on the test panels. The main fouling observed was filamentous algae that hung from the frame of the apparatus, from the clean sections between the test panels, and from some fouled panels.

The extent of fouling was assessed and scored by two independent observers. Statistical controls establish excellent agreement between the observers. The observers scored the control panels as "heavily" fouled after a six-week exposure. At the same time, a total of 8 test panels corresponding to 6 compound-dose-paint formulations showed significantly less growth than the controls. Some test panels remained completely free of algal growth after six-week exposure. Formulations containing T1 ($R_1=C_{10}H_{21}$, $R_3=C_4H_9$, $R_2=H$, $R_4=CH_3$, $X^-=Cl^-$) showed virtually no growth over the first six weeks of the experiment in three different formulations. In two formulations, growth on panels containing G1 ($R_1=C_{14}H_{29}$, $R_3=C_4H_9$, $R_2=R_5=R_6=H$, $X^-=Cl^-$) was inhibited relative to controls during the initial growth period, but increased after five weeks to levels that were less fouled but not statistically significantly relative to controls. These data establish that these compounds inhibit initial growth on the surfaces.

After a 9-month exposure all control panels and untreated surfaces were heavily fouled with brown and green algae, and barnacles had set in many places. Several other organisms inhabited regions of the dense algal mat around and on the painted panels. Several test panels were significantly less fouled than control surfaces with a substantial portion of the surface (>90% in some cases) free of attached algae and barnacles. All formulations containing T1 ($R_1=C_{10}H_{21}$, $R_3=C_4H_9$, $R_2=H$, $R_4=CH_3$, $X-=Cl^-$) showed clear dose dependent anti-fouling activity. The majority of formulations containing G1 ($R_1=C_{18}H_{37}$, $R_3=C_4H_9$, $R_2=R_5=R_6=H$, $X^-Cl^-$) or G1 ($R_1=Cl_{10}H_{21}$, $R_3=R_5=C_4H_9$, $R_2=R_6=H$, $X_-=Cl^-$) also showed dose-dependent anti-fouling activity. These data establish that these compounds inhibit marine growth on treated surfaces, both during the initial colonization phase, and over the longer term.

An experiment was designed to examine the stability of the compounds in seawater over a period of time to determine the rate of microbial degradation of the compound. Seawater samples (20 L) were held at 11° C. in an east-facing window and air was bubbled for 2 hours each day to maintain saturation. Compound T1 ($R_1=C_{10}$ $H_{21}$, $R_2=H$, $R_3=C_4H_9$, $R_4=CH_3$, $X^-=Cl^-$) was added at an initial concentration of 100 nM. At intervals over 5 days, 100 mL samples of seawater were withdrawn and analyzed by electrospray mass spectrometry. A steady decline in the concentration of T1 ($R_1=C_{10}H_{21}$, $R_2=H$, $R_3=C_4H_9$, $R_4=C_4H_9$, $R_4=CH_3$, $X^-=Cl^-$) was an apparent half-life of 80 hours under the experimental conditions. This experiment establishes that the compound is likely to degraded in the environment. The product of the degradation is initially the corresponding urea that is then further degraded by the microorganisms in the seawater.

What is claimed is:

1. A composition comprising a compound selected from the group consisting of compounds having a first formula

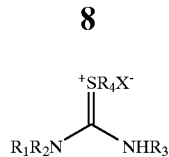

where $R_4$ and at least one of the other $R_1$, $R_2$ or $R_3$ groups are selected independently from the group consisting of alkyl, cycloalkyl, alkenyl, cycloalkenyl, and heteroaryl other than phthalocyanine, the remaining $R_1$, $R_2$ or $R_3$ groups are independently selected from the group consisting of hydrogen, alky, cycloalkyl, alkenyl, cycloalkenyl, and heteroaryl, and $X^-$ is an anion;

compounds having a second formula

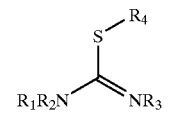

where $R_4$ and at least one of the other $R_1$, $R_2$ or $R_3$ groups are independently selected from the group consisting of alkyl, cycloalkyl, alkenyl, cycloalkenyl, and heteroaryl other than phthalocyanine, and the remaining $R_1$, $R_2$ or $R_3$ groups are independently selected from the group consisting of hydrogen, alkyl, cycloalkyl, alkenyl, cycloalkenyl, and heteroaryl; and mixtures thereof .

2. The composition according to claim 1 where $X^-$ is selected from the group consisting of halide, nitrate, and acetate.

3. The composition according to claim 1 where $R_4$ and at least one of the other $R_1$, $R_2$ or $R_3$ groups are independently selected from the group consisting of alkyl cycloalkyl, alkenyl, and cycloalkenyl, and the remaining $R_1$, $R_2$ or $R_3$ groups are independently selected from the group consisting of hydrogen, alkyl, cycloalkyl, alkenyl, and cycloalkenyl.

4. The composition according to claim 1 where $R_4$ and at least one of the other $R_1$, $R_2$ or $R_3$ groups are alkyl and the remaining $R_1$, $R_2$ or $R_3$ groups are independently selected from the group consisting of hydrogen and alkyl.

5. The composition according to claim 1 where the total number of carbon atoms in selected compounds is between about 8 and about 30.

6. A method for limiting the growth of organisms on a surface, comprising; applying to a surface a compound selected from the group consisting of compounds having a first formula

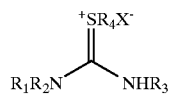

where $R_4$ and at least one of the other $R_1$, $R_2$ or $R_3$ groups are independently selected from the group consisting of alkyl, cycloalkyl, alkenyl, cycloalkenyl, aryl, and heteroaryl, the remaining $R_1$, $R_2$ or $R_3$ groups are independently selected from the group consisting of hydrogen, alkyl, cycloalkyl, alkenyl, cycloalkenyl, aryl, and heteroaryl, and $X^-$ is an anion;

compounds having a second formula

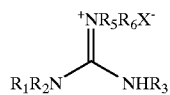

where
R₁, R₂, R₃, R₅, and R₆ are selected such that at least two of the R₁, R₂, R₃, R₅ or R₆ groups are independently selected from the group consisting of alkyl, cycloalkyl, alkenyl, cycloalkenyl, aryl, and heteroaryl, the remaining R₁, R₂, R₃, R₅ or R₆ groups are independently selected from the group consisting of hydrogen, alkyl. cycloalkyl, alkenyl, cycloalkenyl, aryl, and heteroaryl, and X⁻ is an anion;

compounds having a third formula

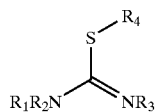

where
R₄ and at least one of the other R₁, R₂ or R₃ groups are independently selected from the group consisting of alkyl, cycloalkyl, alkenyl, cycloalkenyl, aryl, and heteroaryl and the remaining R₁, R₂ or R₃ groups are independently selected from the group consisting of hydrogen, alkyl, cycloalkyl, alkenyl, cycloalkenyl, aryl, and heteroaryl;

compounds having a fourth formula

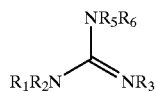

where
at least two of R₁, R₂, R₃, R₅, and R₆ are independently selected from the group consisting of alkyl, cycloalkyl, alkenyl, cycloalkenyl, alkyl, and heteroaryl, and the remaining R₁, R₂, R₃, R₅ or R₆ groups are independently selected from the group consisting of hydrogen, alkyl cycloalkyl, alkenyl, cycloalkyl, aryl, and heteroaryl, and
mixtures thereof.

7. The method according to claim 6 wherein the compound is selected from the group consisting of N,N-disubstituted guanidinium salts, N,N'-disubstituted guanidinium salts, N,N,N'-trisubstituted guanidinium salts, N,N',N"-trisubstituted guanidinium salts, N,N,N',N"-tetrasubstituted guanidinium salts, N,N,N',N',N"-pentasubstituted guanidinium salts, N,N',S-trisubstituted isothiouronium salts, N,N,S-trisubstituted isothiouronium salts, N,N,N',S-tetrasubstituted isothiouronium salts, and mixtures thereof and where the N, N', N", and S substituents are selected from the group consisting of alkyl, cycloalkyl, alkenyl, cycloalkenyl, aryl, and mixtures thereof.

8. The method according to claim 7 wherein the compound is selected from the group consisting of N,N-dialkylsubstituted guanidinium salts, N,N'-dialkylsubstituted guanidinium salts, N,N,N'-trialkylsubstituted guanidinium salts, N,N',N"-trialkylsubstituted guanidinium salts, N,N,N',N"-tetraalkylsubstituted guanidinium salts, N,N,N',N',N"-pentaalkylsubstituted guanidinium salts, N,N',S-trialkylsubstituted isothiouronium salts, N,N,S-trialkylsubstituted isothiouronium salts, N,N,N',S-tetraalkylsubstituted isothiouronium salts, and mixtures thereof.

9. The method according to claim 8 wherein the compounds are selected from the group consisting of N-butyl-N'-decyl-S-methylisothiouronium salts, N-butyl-N'-decylguanidinium salts, N-butyl-N'-tetradecylguanidinium salts, N-butyl-N'-octadecylguanidinium salts, N,N'-dibutyl-N"-decylguanidinium salts, N,N'-dibutyl-N"-tetradecylguanidinium salts, N'-butyl-N"-butyl-N-octadecylguanidinium salts, and mixtures thereof.

10. An anti-fouling coating, comprising
a coating composition; and
a compound selected from the group consisting of compounds having a first formula

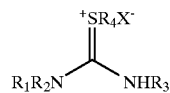

where
R₄ and at least one of the other R₁, R₂ or R₃ groups are independently selected from the group consisting of alkyl, cycloalkyl, alkenyl, cycloalkenyl, and heteroaryl, the remaining R₁, R₂ or R₃ groups are independently selected from the group consisting of hydrogen, alkyl, cycloalkyl, alkenyl, cycloalkenyl, and heteroaryl, and X⁻ is an anion;

compounds having a second formula

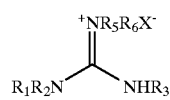

where
at least two of R₁, R₂, R₃, R₅, and R₆ are independently selected from the group consisting of alkyl, cycloalkyl, alkenyl, cycloalkenyl, and heteroaryl, the remaining R₁, R₂, R₃, R₅ or R₆ groups are indepndtly selected from the group consisting of hydrogen, alkyl, cycloalkyl, alkenyl, cycloalkenyl and heteroaryl, and X⁻ is an anion;

compounds having a third formula

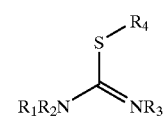

where
R₄ and al least one of the R₁, R₂ or R₃ groups are independently selected from the group consisting of alkyl, cycloalkyl, alkenyl, cycloalkenyl, and heteroaryl and the remaining R₁, R₂ or R₃ groups are independently selected from the group consisting of hydrogen, alkyl, cycloalkyl, alkenyl, cycloalkenyl, and heteroaryl;

compounds having a fourth formula

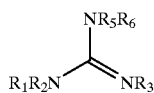

where
at least two of $R_1$, $R_2$, $R_3$, $R_5$, and $R_6$ are independently selected from the group consisting of alkyl, cycloalkyl, alkenyl, cycloalkenyl, and heteroaryl and the remaining $R_1$, $R_2$, $R_3$, $R_5$ or $R_6$ groups are independently selected from the group consisting of hydrogen, alkyl, cycloalkyl, alkenyl, cycloalkenyl, and heteroaryl; and
mixtures thereof.

11. The coating according to claim 10 wherein the compound is selected from the group consisting of N,N-disubstituted guanidinium salts, N,N'disubstitted guanidinium salts, N,N,N'-trisubstituted guanidinium salts, N,N',N"-trisubstituted isothriouronium salts, N,N,N',N"-tetrasubstituted guanidinium salts, N,N,N',N',N"-pentasubstituted guanidinium salts, N,N',S-trisubstituted isothiouronium salts, N,N,S-trisubstituted isothiouronium salts, N,N,N',S-tetrasubstituted isothiouronium salts, and mixtures thereof, where the N, N', N", and S substituents are selected from the group consisting of alkyl, cycloalkyl, alkenyl, cycloalkenyl, aryl, and mixtures thereof.

12. The coating according to claim 11 wherein the compound is selected from the group consisting of N,N-dialkylsubstituted guanidinium salts, N,N'-dialkylsubstituted guanidinium salts, N,N,N'-trialkylsubstituted guanidinium salts, N,N',N"-trialkylsubstituted guanidmum salts, N,N,N',N"-tetraalkylsubstituted guanidinium salts, N,N,N',N',N"-pentaalkylsubstituted guanidinium salts, N,N',S-trialkylsubstituted isothiouronium salts, N,N,S-trialkylsubstituted isothiouronium salts, N,N,N',S-tetraalkylsubstituted isothiouronium salts, and mixtures thereof.

13. The coating according to claim 12 wherein the compounds are selected from the group consisting of N-butyl-N'-decyl-S-methylisothiouronium salts, N-butyl-N'-decylguanidinium salts, N-butyl-N'-tetradecylguanidinium salts, N-butyl-N'octadecylguanidinium salts, N,N'-dibutyl-N"-decylguanidinium salts, N,N'-dibutyl-N"-tetradecylguanidinium salts, N'-butyl-N"-butyl-N-octadecylguanidinium salts, and mixtures thereof.

14. The anti-fouling coating of claim 10 comprising a paint.

15. A compound selected from the group consisting of compounds having a first formula

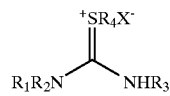

where
$R_4$ and at least one of the other $R_1$, $R_2$ or $R_3$ groups are selected independently from the group consisting of alkyl, cycloalkyl, alkenyl, cycloalkenyl, and heteroaryl other than phthalocyanine, the remaining $R_1$, $R_2$ or $R_3$ groups are independently selected from the group consisting of hydrogen, alkyl, cycloalkyl, alkenyl, cycloalkenyl, and heteroaryl and $X^-$ is an anion;

compounds having a second formula

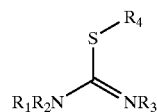

where
$R_4$ and at least one of the other $R_1$, $R_2$ or $R_3$ groups are independently selected from the group consisting of alkyl, cycloalkyl, alkenyl, cycloalkenyl, and heteroaryl other than phthalocyanine, and the remaining $R_1$, $R_2$ or $R_3$ groups are independently selected from the group consisting of hydrogen, alkyl, cycloalkyl, alkenyl, cycloalkenyl, and heteroaryl; and
mixtures thereof.

16. The compound according to claim 15 where $X^-$ is selected from the group consisting of halide, nitrate, and acetate.

17. The compound according to claim 15 where $R_4$ and at least one of the other $R_1$, $R_2$ or $R_3$ groups are independently selected from the group consisting of alkyl, cycloalkyl, alkenyl, cycloalkenyl, and the remaining $R_1$, $R_2$ or $R_3$ groups are independently selected from the group consisting of hydrogen, alkyl, cycloalkyl, alkenyl, and cycloalkenyl.

18. The compound according to claim 15 where $R_4$ and at least one of the other $R_1$, $R_2$ or $R_3$ groups are alkyl, and the remaining $R_1$, $R_2$ or $R_3$ groups are independently selected from the group consisting of hydrogen and alkyl.

19. The compound according to claim 15 where the total number of carbon atoms in selected compounds is between about 8 and about 30.

* * * * *

UNITED STATES PATENT AND TRADEMARK OFFICE
CERTIFICATE OF CORRECTION

| | | |
|---|---|---|
| PATENT NO. | : 6,518,309 B1 | |
| APPLICATION NO. | : 09/548666 | |
| DATED | : February 11, 2003 | |
| INVENTOR(S) | : Fyles et al. | |

It is certified that error appears in the above-identified patent and that said Letters Patent is hereby corrected as shown below:

In the Title:

"MICROBIOCIDAL PROPERTIES OF POY-SUBSTITUTED ... SALTS)"

should read -- MICROBIOCIDAL PROPERTIES OF POLY-SUBSTITUTED GUANIDINIUM SALTS (ALSO AS: MICROBIOCIDAL PROPERTIES OF SUBSTITUTED ISOTHIOURONIUM SALTS AND POLY-SUBSTITUTED GUANIDINIUM SALTS) --

Signed and Sealed this

Twentieth Day of March, 2007

JON W. DUDAS
*Director of the United States Patent and Trademark Office*